United States Patent [19]

Powell et al.

[11] Patent Number: 5,059,721
[45] Date of Patent: Oct. 22, 1991

[54] PROCESS FOR PREPARING A BISPHENOL

[75] Inventors: Joseph B. Powell; Zaida Diaz, both of Houston, Tex.

[73] Assignee: Shell Oil Company, Houston, Tex.

[21] Appl. No.: 560,956

[22] Filed: Jul. 31, 1990

[51] Int. Cl.$^5$ .................. C07C 37/20; C07C 37/70; C07C 39/14
[52] U.S. Cl. ............................ 568/724; 568/727
[58] Field of Search ............... 568/722, 724, 728, 727

[56] References Cited

U.S. PATENT DOCUMENTS

| | | | |
|---|---|---|---|
| 4,160,110 | 7/1979 | Carnahan, Jr. ................ | 568/703 |
| 4,169,211 | 9/1979 | Ligorati et al. ............... | 568/724 |
| 4,396,728 | 8/1983 | Faler ........................... | 521/32 |
| 4,469,561 | 9/1984 | Sikdar et al. ................. | 203/39 |
| 4,533,764 | 8/1985 | Chang et al. ................. | 568/724 |
| 4,766,254 | 8/1988 | Faler et al. .................... | 568/724 |
| 4,847,433 | 7/1989 | Kissinger ....................... | 568/727 |
| 4,906,789 | 3/1990 | Grzywa .......................... | 568/727 |

Primary Examiner—Werren B. Lone

[57] ABSTRACT

In a process for the preparation of a bisphenol by condensation of a phenolic compound and a carbonyl compound in the presence of an acidic ion exchange resin catalyst, strong acids that leach from the acidic ion exchange resin catalyst into the reaction effluent are scavenged by a carbon adsorbent. The acid scavenging improves the product quality and yield by reducing acid catalyzed cracking of bisphenols during purification and finishing steps.

7 Claims, 2 Drawing Sheets

○ WATER SOLVENT
□ PHENOL SOLVENT

△ HPLC ASSAY FOR PSA
□ ACID TITRATION

PROCESS FOR PREPARING A BISPHENOL

BACKGROUND OF THE INVENTION

This invention relates to the preparation of a bisphenol. In one aspect, the invention relates to improving purity and yield in a process to manufacture a bisphenol employing an acidic ion exchange resin catalyst.

Bisphenols are used as the starting material in the manufacture of resins such as polycarbonate resins and epoxy resins. It is important that the bisphenol starting material is as pure as possible in order to avoid adverse effects on the properties of resulting resins.

Bisphenols can be manufactured over a strongly acidic ion exchange resin catalyst by condensation of a phenol and a ketone or an aldehyde. If a sulfonated organic polymer is used as the acidic ion exchange resin catalyst, strong organic acids such as phenol sulfonic acid have been found to leach into the reaction product mixture. As an example, typically for bisphenol-A (BPA), the product stream from the reaction zone containing BPA in solution is passed to a crystallization zone, wherein the BPA is crystallized as an adduct with phenol and the remaining solution, or "mother liquor," is recycled to the reaction zone. The leached acid will remain in the separated product stream with the crystallized BPA and cause degradation of the BPA product during subsequent process steps, particularly if thermal finishing steps are involved. It has been found that the soluble acid leached from the acidic ion exchange resin acts as a catalyst for cracking of BPA during the thermal finishing step, which results in a lower product purity and a decrease in product yield.

In order to obtain bisphenols with higher purity, it is known to use an amine-based organic anion exchange resin to remove acidic impurities from the mother liquor. Such amine-based resins are expensive and inherently less stable than the catalyst resin, and their use can result in the presence of soluble amines or the reaction products of these amines with phenol in the product stream, which will decrease product quality. When the amine-based resin is used in a recycled system, the soluble amines will in turn poison the acidic ion exchange catalyst upon recycle of unconverted reactant. Such amine-based organic resins are typically regenerated by aqueous base, which is also a poison for the acidic ion exchange resin catalyst.

It is therefore an object of the present invention to provide an acidic ion exchange resin catalyzed bisphenol preparation process with improved purity and yield. It is another object of the present invention to provide a process to remove acidic impurities from a recycled system without poisoning the acidic ion exchange resin catalyst.

SUMMARY OF THE INVENTION

According to the invention, a process for the production of a bisphenol is provided, the process comprising the steps of:

(A) contacting a carbonyl compound with a stoichiometric excess of a phenolic compound in the presence of an effective amount of an acidic ion exchange resin catalyst to produce a reaction product mixture comprising a bisphenol and a sulfonic acid;

(B) contacting the reaction product mixture comprising a bisphenol and a sulfonic acid with a carbon adsorbent under conditions effective to reduce the acidity of the reaction product mixture; and (C) recovering bisphenol from the thus treated reaction product mixture.

DETAILED DESCRIPTION OF THE INVENTION

Figure 1:
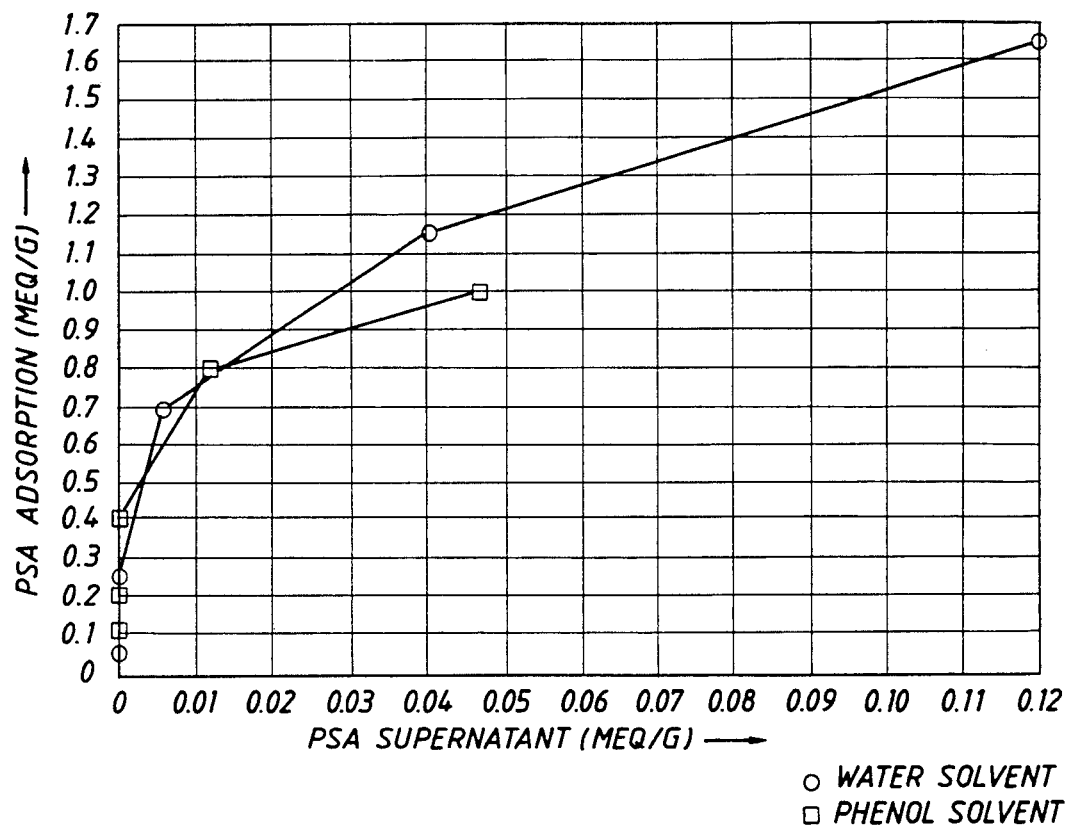
FIG. 1 is a graph of isotherms for adsorption of phenol sulfonic acid on a carbon adsorbent.

According to the invention, a high purity bisphenol can be produced in high yield by contacting a reaction product mixture containing a bisphenol with a carbon guard bed. The reaction product mixture is the effluent of a reaction zone wherein a carbonyl compound and a phenolic compound are allowed to react in the presence of an effective amount of an acidic ion exchange resin catalyst.

The phenolic compounds employed as the starting material in the production of bisphenols according to the invention are any compounds containing a hydroxy group linked to a carbon of an aromatic group. Suitable phenolic compounds include, for example, phenols and substituted phenols, such as: phenol, cresols, xylenols, chlorophenols, thymol, carvacrol, cumenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiary-butylphenol, 4-methyl-2-tertiary-butylphenol, 2-tertiary-butyl-4-methylphenol, 2,3,5,6-tetramethylphenols, 2,6-dimethylphenol, 2,6-ditertiary-butylphenol, 3,5-dimethylphenol, 3,5-diethylphenol, 2-methyl-3,5-diethylphenol, o-phenylphenol, p-phenylphenol, the naphthols, phenanthrol, their homologues and analogues. Suitable phenolic compounds include those containing one or more phenolic groups in each nucleus as well as polynuclear compounds.

The carbonyl compounds employed as the starting material can be any compound of the following formula:

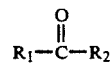

wherein $R_1$ can be any aliphatic, cycloaliphatic, aromatic or heterocyclic radical, and $R_2$ can be hydrogen or an aliphatic, cycloaliphatic, aromatic or heterocyclic radical. Suitable carbonyl compounds include ketones and aldehydes. Examples of suitable ketones include, for example, acetone, 1,3-dichloroacetone, dimethyl ketone, methyl ethyl ketone, diethyl ketone, dibutyl ketone, methyl isobutyl ketone, cyclohexanone, propionylphenone, methyl amyl ketone, mesityl oxide, cyclopentanone, acetophenone, and examples of suitable aldehydes include acetaldehyde, propionaldehyde, butyraldehyde and benzaldehyde.

The specific phenolic compound and carbonyl compound employed as starting material will depend upon the specific bisphenol compound desired and may be governed to some extent by specific operating conditions employed. The invention process is particularly suitable for production of bisphenol-A, for which the carbonyl compound is acetone and the phenolic compound is phenol. Typically, excess phenol is used for the condensation reaction. Preferably the ratio of phenol to carbonyl compound is within the range of about 20:1 to 2:1, generally about 12:1 to 2:1.

Acidic ion exchange resins usable in the condensation reaction of a phenolic compound and a carbonyl compound according to the present invention include essentially all known acidic ion exchange resins. Sulfonated resins are generally preferred. In particular, a sulfonated aromatic organic polymer as the ion exchange resin catalyst is quite suitable.

Various acidic ion exchange resins are disclosed, for example, in U.S. Pat. Nos. 2,597,438, 2,642,417, 3,172,916, 3,394,089, 3,634,341, 4,045,379, 4,396,728, 4,455,409 and 4,584,416. Some examples of suitable commercially available sulfonated resins are: M-31 and G-26 manufactured by Dow Chemical Company; A-15, A-31, A-32, XE-383 and XE-386 manufactured by Rohm and Haas; and SC-102 and SC-104 manufactured by Bayer-Lewatit.

The reaction is preferably executed in the presence of an added promoter for the acid-catalyzed reaction. Any known promoters for the acid catalyzed condensation of a phenolic compound and a carbonyl compound are suitable. Suitable promoters are mercaptan groups which are either free or bound to the resin. An alkyl mercaptan and bis-mercapto ethanolamine are examples of suitable promoters for the invention process.

In order to obtain bisphenols with improved yields and higher purities according to the invention process, the effluent of the reaction zone is contacted with a carbon adsorbent under conditions effective to reduce the acidity of the effluent. A portion of the excess phenol is optionally removed by flashing prior to or after the acid removal step. The preferred adsorbents are any carbons that exhibit a reasonable surface area and porosity to act as a viable adsorbent in a liquid-phase system. The carbon adsorbent can be in any shape or form. The particle size is preferably within the range of about 0.4 to 2.4 mm diameter, and the surface area is preferably greater than about 50 m$^2$/g. The pore sizes typically range from about 20 to 1000 angstroms. Preferred carbons exhibit a low ash content, or are acid washed to remove leachable metal contaminants prior to use. The carbon should also be prewashed with demineralized water to remove fines before use. Typical carbons may be derived from coal, coconuts, wood, bone char, peat, or any other suitable source of carbon. Alternatively, a carbon layer may be deposited on a suitable non-carbon carrier. A suitable binder may optionally be used to maintain integrity of the carbon particle. Activation or calcination of the carbon may optionally be employed. The preferred carbon is prepared from a bituminous coal, calcined with a suitable binder, and acid washed before use.

The effluent is preferably contacted with a fixed-bed activated carbon in either an upflow or downflow configuration at a weight hourly space velocity (WHSV) within the range of about 0.2 to 10, preferably about 0.5 to 3. If an upflow mode is employed, the bed should not be fluidized so that back mixing and fines generation are minimized. The WHSV in the acid scavenging zone may vary considerably within the scope of the invention depending to some extent upon the specific bisphenol products, the catalyst, the acid loss rate from the reaction and the adsorbent used, but is preferably within the range of about 0.2 to 10 in order to obtain acid concentrations of less than about 0.1 ppm in the effluent after treatment.

For convenience, the invention process will be specifically described in terms of its most preferred embodiment, in which acetone and an excess of phenol are contacted in a reaction zone in the presence of a sulfonated cationic exchange resin catalyst and free mercaptan to produce BPA. The reaction is carried out in one or a series of reactors operated at temperatures within the range of about 60° to about 95° C. The reaction effluent includes bisphenol-A, acetone, water, mercaptan, phenol, various phenolic by-products of the reaction, and acids leached from the catalyst. After removing a portion of excess phenol by flashing, the effluent is passed through a fixed-bed carbon adsorbent to remove heavy or non-volatile acids (e.g. sulfonic acids and sulfuric acid) at temperatures within the range of about 65° to about 130° C. In an optional embodiment of the invention process, the acid removal step can be carried out prior to the flashing step.

Subsequently, BPA can be purified and removed from the adsorbent-treated effluent by various methods. Suitable means for recovering bisphenols include one or more of such steps as, distillation, solvent extraction, stratification, extractive distillation, adsorption, crystallization, filtration, centrifugation and thermal liberation. Typically, the BPA is isolated by passing the treated reaction product stream containing BPA to a crystallization zone, where the stream is cooled to crystallize a BPA-phenol adduct or treated with water to crystallize the BPA. Slurries of crystallized BPA or crystalline adducts of BPA are separated from the remaining solution by filtration or by centrifugation and the remaining filtrate or "mother liquor" is recycled to the reaction zone. In a finishing zone, BPA isolated as a crystalline adduct is converted to BPA by thermally stripping phenol from the adduct and recrystallizing, and the water-crystallized BPA is dried. More than one such step can be employed in the finishing zone to purify BPA. Subsequently, the purified BPA is recovered.

In an optional embodiment of the invention process, the acid removal step is carried out downstream of the crystallization step before recovery of the BPA.

Bisphenols prepared by the invention process have improved purity and yield, as thermal cracking of the product is minimized or eliminated. The invention process provides a conveniently recyclable system without significant risk of contamination of the acidic ion exchange resin catalyst. This is advantageous particularly in a system in which the mother liquor is recycled to the reactor.

The following examples demonstrate the acid removal step in a bisphenol production process according to the invention process.

EXAMPLE 1-2

Phenol doped with varying known concentrations of phenol sulfonic acid was contacted with an activated carbon (CALGON, TYPE CAL) prepared from a bituminous coal and calcined with a binder before acid washing with HCl. The activated carbon was first water washed and dried in a vacuum oven at 90° C. before use. The ratio of phenol supernatant to carbon adsorbent was 20:1. The carbon/phenol mixtures were placed in a shaking water bath and allowed to equilibrate at 90° C. for 36 hours. Final concentration of acid in the supernatant was determined by potentiometric titration with 0.01 or 0.1N potassium hydroxide. The amount of acid adsorbed by the carbon was calculated from known initial and measured final supernatant acid concentrations, and the known ratio of supernatant to carbon. Results are shown in FIG. 1. The Langmuir-like curvature (concave downward) is indicative of strong adsorption of the acid by carbon.

The experiment was repeated with water as a supernatant at 25° C. The resulting adsorption isotherm was quite similar to that obtained in dry phenol at 90° C. This result indicates the adsorption is not sensitive to temperature or phenol/water ratio. The strong adsorption evident from the curvature of the isotherms in FIG. 1 indicates the carbon adsorbent will give a favorable performance if implemented in a fixed bed to adsorb acid in a continuous flow process.

EXAMPLE 3

Figure 2:
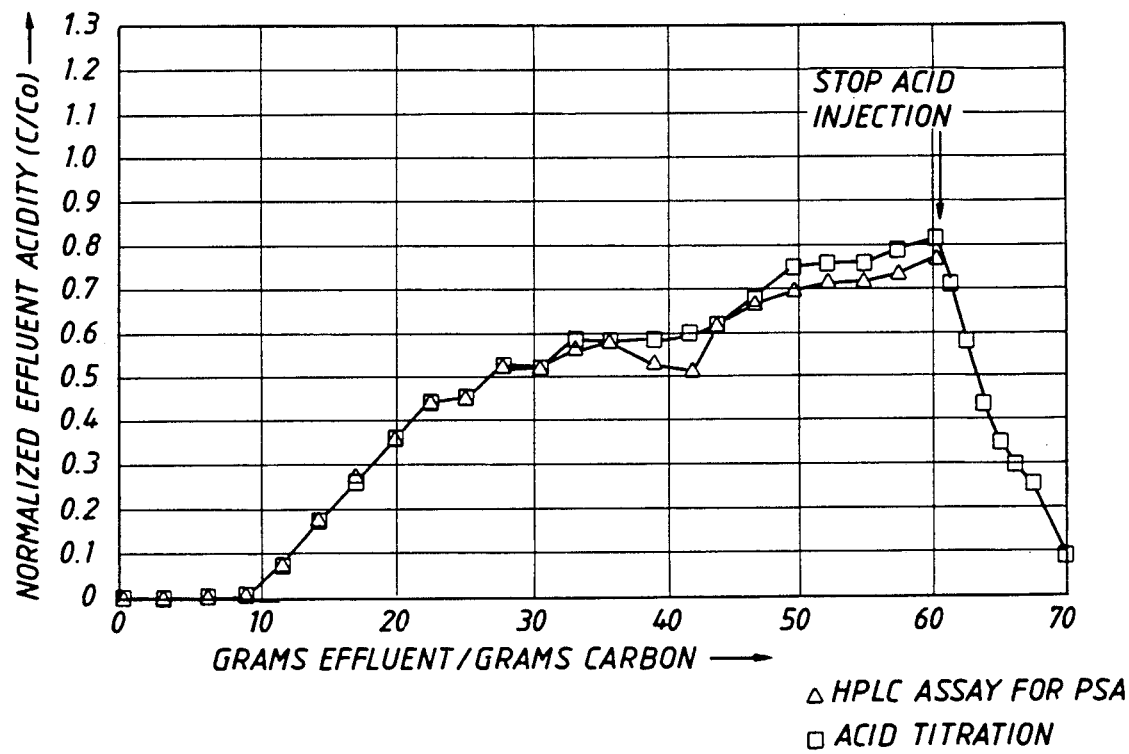
FIG. 2 is a graph of the results of a flow demonstration of acid removed by activated carbon of Example 3.
Figure 3:
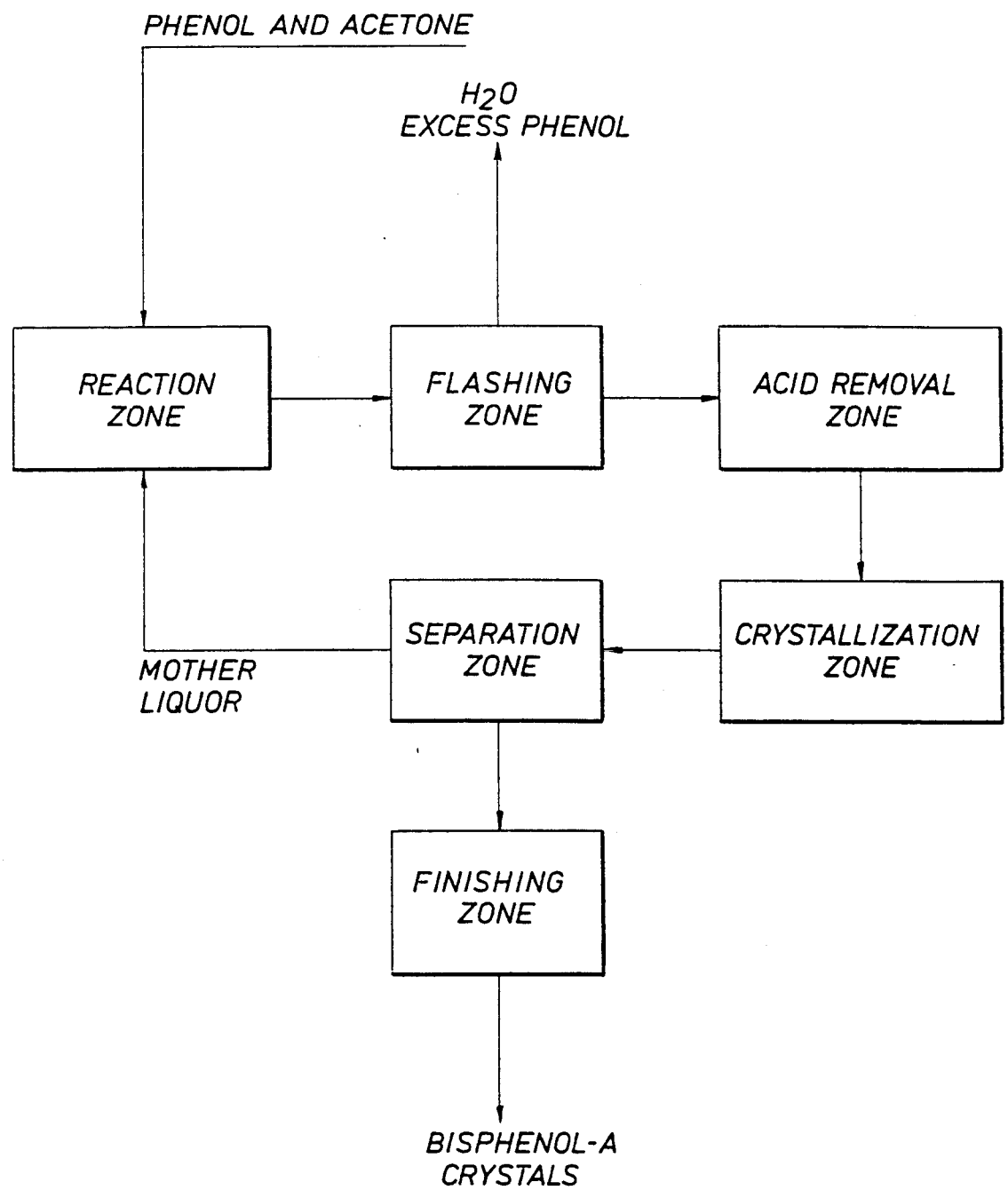
FIG. 3 is a schematic flow diagram illustrating the most preferred embodiment of the invention process.

A packed bed containing 36 grams of the above carbon was water washed. Phenol containing 2207 ppmw of phenol sulfonic acid (PSA) was passed over the bed at 90° C. at a weight hourly space velocity (WHSV), defined as grams of effluent per gram of carbon per hour, of 10.5. FIG. 2 shows acidity in the effluent (normalized by the 2207 ppmw injected concentration) versus the cumulative amount of effluent collected normalized by the total weight of carbon, or the "bed weights+ of effluent produced. Effluent acidities were determined by potentiometric titration of effluent samples. These values were confirmed via analysis of PSA by liquid chromatography.

No acid was observed in the effluent until ten bed weights of effluent had been produced, while the effluent concentration did not exceed 50% of the injected concentration until more than 20 bed weights of effluent had been produced. If no adsorption had occurred, the injected concentration of acid would have appeared in the effluent after production of only one bed weight of effluent. The flow experiment thus demonstrates efficient and virtually complete acid removal by the carbon adsorbent, as expected from the isotherm studies of examples 1 and 2. It is known that by reducing weight hourly space velocity, breakthrough of acid can be further delayed, such that the "equilibrium+ breakthrough at 64 bed weights (calculated from the above isotherm) can be approached.

EXAMPLES 4–6

One gram of bisphenol-A was doped with varying amounts of phenol sulfonic acid (PSA) to give the concentrations reported in Table 1. Each sample was sealed in a glass ampoule and heated at 180° C for 30 minutes to simulate temperatures found in thermal finishing of BPA. Contents of the ampoule were then dissolved in acetonitrile solvent for analysis by liquid chromatography. The assay was specific for phenol and isopropenyl phenol (IPP), which are known products of the acid-catalyzed degradation of Bisphenol-A. The amounts of undesired phenol and IPP formed in these tests increased with increasing acid content of the sample. These results demonstrate the sensitivity of the process to trace concentrations of phenol sulfonic acid. Concentrations of phenol and IPP in BPA product above 100 ppmw are undesirable. The importance of removal of this acid with the carbon adsorbent is thus demonstrated.

TABLE 1

| CRACKING OF BISPHENOL-A CATALYZED BY PHENOL SULFONIC ACID 30 MINUTES, 180° C., SEALED AMPOULES | | | |
|---|---|---|---|
| Run | Acid ppm | Phenol (ppmw) | IPP (ppmw) |
| Example 4 | 5.8 | 1400 | 357 |
| Example 5 | 0.5 | 80 | 47 |
| Example 6 | 0 | 28 | 16 |
| Feed | 0 | 25 | 16 |

Example #6 = Blank
IPP = Isopropenyl Phenol
Feed = Unheated BPA Feed Sample Assay

EXAMPLE 7

Phenol was recirculated continuously through a 38-gram packed bed containing a sulfonic acid ion exchange resin catalyst followed by a 35-gram packed bed of the activated carbon adsorbent described above at 80° C. and at a WHSV of 3. Effluent samples from the catalyst bed contained 0.6 ppmw phenol sulfonic acid, at steady state, as determined by liquid chromatography. No acidity was detected in the effluent from the carbon bed at any time during 38 days of continuous operation. Using the 0.6 ppmw loss rate from the catalyst bed, a concentration of 17 ppmw PSA is calculated as the concentration of acid that would have been realized in the closed recirculation system, if acid were not removed by the carbon adsorbent. The deleterious impact of acid concentrations between 0.6 ppmw and 17 ppmw on bisphenol-A product quality is evident from examples 4-6.

We claim:
1. A process for the production of bisphenol comprising the steps of:
   (a) contacting, in a reaction zone, a carbonyl compound selected from the group consisting of ketones and aldehydes with a stoichiometric excess of a phenolic compound in the presence of an effective amount of an acidic ion exchange resin catalyst under conditions effective to produce a reaction product mixture comprising a bisphenol and a sulfonic acid;
   (b) passing the reaction product mixture containing the bisphenol and the sulfonic acid in contact with a carbon adsorbent and producing an adsorbent-treated disphenol-containing reaction product stream having a lower sulfonic acid content than the reaction product mixture; and
   (c) recovering bisphenol from the adsorbent-treated reaction product stream.
2. The process of claim 1 wherein the carbonyl compound is an aldehyde.
3. The process of claim 1 wherein the carbonyl compound is a ketone.
4. The process of claim 3 wherein the ketone is acetone.
5. The process of claim 1 wherein the reaction product mixture is contacted with carbon adsorbent at temperatures within the range of from about 65° C. to about 130° C.
6. The process of claim 1 in which step (c) comprises subjecting the carbon adsorbent-treated reaction product stream to conditions effective for crystallization of a bisphenol/phenol adduct from a mother liquor and recovering the bisphenol from the bisphenol/phenol adduct.
7. The process of claim 6 which further comprises passing at least a portion of the mother liquor to the reaction zone.

* * * * *